(12) United States Patent
Wu et al.

(10) Patent No.: US 10,968,439 B2
(45) Date of Patent: Apr. 6, 2021

(54) XYLANASE MUTANT

(71) Applicant: QINGDAO VLAND BIOTECH GROUP CO., LTD, Shandong (CN)

(72) Inventors: Xiuxiu Wu, Shandong (CN); Chao Shao, Shandong (CN); Yijun Huang, Shandong (CN)

(73) Assignee: QINGDAO VLAND BIOTECH GROUP CO., LTD, Shandong (CN)

( * ) Notice: Subject to any disclaimer, the term of this patent is extended or adjusted under 35 U.S.C. 154(b) by 0 days.

(21) Appl. No.: 16/639,571

(22) PCT Filed: Apr. 19, 2018

(86) PCT No.: PCT/CN2018/083635
§ 371 (c)(1),
(2) Date: Feb. 16, 2020

(87) PCT Pub. No.: WO2019/033775
PCT Pub. Date: Feb. 21, 2019

(65) Prior Publication Data
US 2020/0239865 A1    Jul. 30, 2020

(30) Foreign Application Priority Data
Aug. 18, 2017 (CN) .......................... 2017 1 0712383

(51) Int. Cl.
*C12N 9/24* (2006.01)
*C12N 15/80* (2006.01)
*C12N 15/63* (2006.01)
*C12N 15/81* (2006.01)

(52) U.S. Cl.
CPC ......... *C12N 9/2482* (2013.01); *C12N 15/815* (2013.01); *C12Y 302/01008* (2013.01)

(58) Field of Classification Search
CPC ....... C12N 9/248; C12N 9/2482; C12N 15/00
See application file for complete search history.

(56) References Cited

FOREIGN PATENT DOCUMENTS

| CN | 102757947 A | 10/2012 |
|---|---|---|
| CN | 104630183 A | 5/2015 |
| CN | 104911163 A | 9/2015 |
| WO | 9424270 A2 | 10/1994 |

OTHER PUBLICATIONS

International Search Report for PCT/CN2018/083635 dated Jul. 16, 2018, ISA/CN.

*Primary Examiner* — Maryam Monshipouri
(74) *Attorney, Agent, or Firm* — Yue (Robert) Xu; Apex Attorneys at Law, LLP

(57) ABSTRACT

The present invention relates to the technical field of protein engineering, and, in particular, to a xylanase mutant with improved heat tolerance. The present invention artificially introduces two or three unnatural disulfide bridges into xylanase by site-directed mutagenesis and obtains the mutants XynA1 and XynA2 with improved heat tolerance, especially the mutant XynA2 into which three disulfide bridges are introduced, achieving residual enzyme activity of 75% after treatment at 80° C. for 5 min, 72% higher than the residual enzyme activity of the mutant XynA1. The present invention further obtains, by screening, three mutation sites Q51N, H143K, and Q161F that can significantly increase the heat tolerance of mutants, and introduction of the mutation sites into the XynA1 and XynA2 xylanases, whether at a single point or a combination of two points or a combination of three points, can effectively improve the heat tolerance of the mutants.

8 Claims, No Drawings
Specification includes a Sequence Listing.

XYLANASE MUTANT

CROSS REFERENCE TO RELATED APPLICATIONS

This application is a US National Phase application based upon PCT Application No. PCT/CN2018/083635, filed Apr. 19, 2018, which claims priority to Chinese application No. 201710712383.9, titled with "Xylanase mutant", filed on Aug. 18, 2017, and the contents of which are fully incorporated herein by reference.

FIELD

This invention relates to protein engineering field, and particularly relates to xylanase mutants with improved heat resistance.

BACKGROUND

Xylan is a major component of hemicellulose in plant and is widely found in agricultural residue such as corn cob, bagasse, wheat bran and straw. Xylanase can degrade xylan into xylooligosaccharide and xylose of various lengths, which has important economic value. More and more researches are focused on xylanase, through which these available resources can be fully utilized to maximize its potential application value.

Xylanase is a type of glycosyl hydrolases which is able to hydrolyse β-1, 4-linked xylopyranoside chains. Xylanase has been found in at least one hundred different organisms and can be produced economically on an industrial scale. Xylanase and other glycosyl hydrolases form a superfamily which includes more than 40 different enzyme families. *Trichoderma reesei* can produce three different xylanases of which xylanases I and II (XynI and XynII) are with the best characteristics. The molecular weight of XynI is 19 kDa, and the isoelectric point and pH optimum of XynI (pI 5.5, pH 3-4) are all lower than XynII, of which the molecular weight is 20 kDa, the isoelectric point is 9.0, and the pH optimum is 5.0-5.5.

Xylanase has been widely used in pulp bleaching, modification of textile fibres, and the production of animal feed and human foods. The main problems restricting the application of xylanase are the extreme conditions. High temperature and the pH in industrial application which is different from the optimal pH of xylanase will decrease the effective utility of xylanase.

In the process of pulp bleaching, the materials after alkaline wash are in high temperature (>80° C.) and pH (>10). Most of the xylanases will be inactivated in these conditions. So the pulp must be cooled and neutralized before adding xylanase which will increase the cost.

In the process of feed production, there is a short period with high temperature (e.g. 2-5 min at 90° C.). However, xylanase has catalytic activity at lower temperature (e.g. 37° C.). Therefore, xylanase will be inactivated irreversibly at high temperature.

Although the stability of xylanase has been improved in a lot of research, it still cannot meet the requirements. Therefore, it is of great importance to provide a thermostable xylanase suitable for industrial applications.

SUMMARY

This invention provides a xylanase mutant. The thermostability of the phytase mutant is significantly improved, which is conducive to the wide applications of the xylanase mutant in feed field.

In order to achieve the above object, this invention provides the technical solutions as follows.

This invention provides a xylanase mutant comprising one or more disulfide bridges selected from the group consisting of T1C-T27C, Q33C-T187C and S109C-N153C (according to the position in the sequence of xylanase);

and the xylanase mutant comprises an amino acid sequence selected from (I), (II) and (III):

(I) an amino acid sequence having at least 95% identity to the amino acid sequence of SEQ ID NO:1;

(II) an amino acid sequence having at least one immune epitope of the xylanase, and a modification, substitution, deletion or insertion of one or more amino acids within the amino acid sequence of SEQ ID NO:1;

(III) an amino acid sequence encoded by a nucleotide sequence of SEQ ID NO: 2 or the complementary sequence thereof, or a nucleotide sequence encoding the same amino acid sequence but having a different sequence from SEQ ID NO: 2 or the complementary sequence thereof due to the degeneracy of genetic code;

wherein the substitution is one or more amino acid substitution(s) in a position selected from positions 51, 143 and 161.

In some embodiments of the invention, the xylanase mutant comprises amino acid sequence which has at least 96% identity to the amino acid sequence of xylanase.

In some embodiments, the xylanase mutant comprises amino acid sequence which has at least 97% identity to the amino acid sequence of xylanase.

In some embodiments, the xylanase mutant comprises amino acid sequence which has at least 98% identity to the amino acid sequence of xylanase.

In some embodiments, the xylanase mutant comprises amino acid sequence which has at least 99% identity to the amino acid sequence of xylanase.

In some embodiments, the xylanase mutant comprises one or more than one disulfide bridges selected from T1C-T27C, Q33C-T187C and S109C-N153C.

In some embodiments, the xylanase mutant comprises two or three disulfide bridges selected from T1C-T27C, Q33C-T187C and S109C-N153C.

In some embodiments, the xylanase mutant comprises two disulfide bridges: Q33C-T187C and S109C-N153C.

In some embodiments, the xylanase mutant comprises three disulfide bridges: T1C-T27C, Q33C-T187C and S109C-N153C.

In some embodiments, the xylanase mutant has amino acid sequence shown as SEQ ID NO: 3 or SEQ ID NO: 5.

The invention also provides a DNA molecule encoding the xylanase mutant.

In some embodiments, the DNA molecule encoding xylanase mutant has polynucleotide sequence shown as SEQ ID NO: 4 or SEQ ID NO: 6.

In other embodiments, the xylanase mutant comprises at least one amino acid substitution in the position selected from positions 51, 143 and 161, the positions corresponding to the respective position in the amino acid sequence of the xylanase.

In other embodiments, the xylanase mutant comprises at least two amino acid substitutions in the position selected from positions 51, 143 and 161, the positions corresponding to the respective position in the amino acid sequence of the xylanase.

In other embodiments, the xylanase mutant comprises three amino acid substitutions in the positions 51, 143 and 161, the positions corresponding to the respective position in the amino acid sequence of the xylanase.

In the preferred embodiments, the xylanase mutant comprises at least one amino acid substitution selected from Q51N, H143K and Q161F.

In other embodiments, the xylanase mutant comprises an amino acid sequence selected from SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

The invention also provides a DNA molecule encoding the xylanase mutant above.

In some embodiments, the DNA molecule encoding the xylanase mutant comprises a polynucleotide sequence selected from SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

The invention also provides a vector containing the DNA molecule encoding xylanase mutant.

The invention also provides a host cell containing the recombinant expression vector.

In some embodiments, the host cell is *Pichia*.

The thermostability of the recombinant xylanase mutant expressed in *Pichia* is significantly improved.

This invention provides two xylanase mutants, XynA1 and XynA2, which comprise two and three extra disulfide bridges, respectively. The thermostability of the mutants are significantly improved, especially the mutant XynA2 with three extra disulfide bridges. After being treated at 80° C. for 5 min, the residual activity of the mutant XynA2 is 75%, which is 72% higher than that of the mutant XynA1. Furthermore, this invention provides three point mutations Q51N, H143K and Q161F by screening, which can improve the thermostability of the mutants. The thermostability of the mutant XynA1 can be significantly improved by introducing one or two or three mutations selected from Q51N, H143K and Q161F. Especially, the introduction of the combination of three mutations XynA1-H143K-Q51N-Q161F gives a residual enzyme activity of the mutant up to 61.28% after being treated at 80° C. for 5 min and 26.89% after being treated at 85° C. for 3 min, showing an excellent thermostability. When single point mutation of the above three point mutations is introduced into XynA2, the residual activity of the mutant is increased by 9.26%-24.58% after being treated at 80° C. for 5 min and by 26.63%-46.61% after being treated at 85° C. for 3 min. Furthermore, when two or three mutations are introduced into XynA2, the following mutation combinations show better heat resistance than the one comprising single mutation. The combinations are H143K+Q161F, Q51N+Q161F and H143K+Q51N+Q161F. The residual activities of the mutants with the combinations is 100% after being treated at 80° C. for 5 min and over 95% after being treated at 85° C. for 3 min.

DETAILED DESCRIPTION

The invention discloses a xylanase mutant. Technicians having ordinary skill in the field can learn from the contents of this invention and improve the process parameters to realize it. It is particularly to be noted that all similar substitutions and modifications will be regarded as obvious and are considered to be included in the invention. The invention has described the methods and applications in the preferred embodiments, and technicians in this field can readily modify or appropriately modify and combine the methods and applications to realize and apply the invention without departing from the contents, spirit and scope of the invention.

The invention will now be described in detail by way of reference only using the following definitions and examples. Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale &Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acid sequences are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole.

Practitioners are particularly directed to Sambrook et al., 1998, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

As used herein, the term "polypeptide" refers to a compound made up of a single chain of amino acid residues linked by peptide bonds. The term "protein" herein may be synonymous with the term "polypeptide" or may refer, in addition, to a complex of two or more polypeptides.

As used herein, the term "expression" refers to the process by which a polypeptide is produced based on the nucleic acid sequence of the gene. The process includes both transcription and translation.

As used herein, the term "gene" means the segment of DNA involved in producing a polypeptide chain, that may or may not include regions preceding or following the coding region.

As used herein, the term "disulphide bridge" or "disulphide bond" refers to the bond formed between the sulphur atoms of cysteine residues in a polypeptide or a protein. In this invention, a disulphide bridge or disulphide bond may be introduced by way of point mutation.

As used herein, an "enzyme" refers to a protein or polypeptide that catalyzes a chemical reaction.

As used herein, the term "activity" refers to a biological activity associated with a particular protein, such as enzymatic activity associated with a protease. Biological activity refers to any activity that would normally be attributed to that protein by one skilled in the art.

As used herein, the term "xylanase" refers to glycosyl hydrolases that hydrolyse β–1, 4-linked xylopyranoside chains.

As used herein, "wild-type" refers to a sequence or a protein that is native or naturally occurring.

As used herein, "point mutations" refers to a change in a single nucleotide of DNA, especially where that change shall result in a change in a protein.

As used herein, "mutant" refers to a version of an organism or protein where the version is other than wild-type. The change may be affected by methods well known to one skilled in the art, for example, by point mutation in which the resulting protein may be referred to as a mutant.

As used herein, "modified" refers to a sequence, such as an amino acid sequence comprising a polypeptide which includes a deletion, insertion, replacement or interruption of a naturally occurring sequence.

As used herein, "substituted" refers to the replacement of a naturally occurring residue.

As used herein, "thermostable" refers to the quality of being stable in an atmosphere involving temperature. For example, a thermostable organism is one that is more stable under specified temperature conditions than a non-thermostable organism.

As used herein, "thermostability," refers to the quality of being thermostable.

As used herein, "α-helix" refers to the structure that results when a single polypeptide chain turns regularly about itself to make a rigid cylinder in which each peptide bond is regular hydrogen-bonded to other peptide bonds in the nearby chain.

The experimental materials and reagents used in a preferred embodiment of the invention.

Strains and vectors: *E. coli* DH5α, *Pichia pastoris* strain GS115, vector pPIC9k, Amp and G418 were purchased from Invitrogen.

Enzymes and kits: PCR enzymes and ligases were purchased from Takara; restriction endonucleases were purchased from Fermentas; plasmid mini kit and gel extraction kit were purchased from Omega; GeneMorph II random mutagenesis kit was purchased from MBL Beijing Biotech Co., Ltd.

Medium Recipes

Luria broth (LB medium): 0.5% yeast extract, 1% tryptone, 1% NaCl, pH 7.0.

LB-AMP medium: LB medium with 100 μg/mL ampicillin.

Yeast extract peptone dextrose medium (YPD medium): 1% yeast extract, 2% tryptone, 2% glucose.

Minimal dextrose medium (MD medium): 2% glucose, 2% agar, 1.34% YNB, $4 \times 10^{-5}$ biotin.

BMGY medium: 2% tryptone, 1% yeast extract, 100 mM potassium phosphate buffer (pH 6.0), 1.34% YNB, $4 \times 10^{-5}$ biotin, 1% glycerol.

BMMY medium: 2% tryptone, 1% yeast extract, 100 mM potassium phosphate buffer (pH 6.0), 1.34% YNB, $4 \times 10^{-5}$ biotin, 1% methanol.

The materials and reagents used for the xylanase mutants provided by the invention can be purchased from the market.

The invention was further illustrated by the following examples:

Example 1 Xylanse Gene Amplification

Xyn-F1:5'-CGC GAATTCACTATTCAACCTGGAACTGGATAC-3' (Underlined was the recognition site of restriction endonuclease EcoR I).

Xyn-R1:5'-CT CGCGGCCGCTTATGAGACTGTGATAGAGGCAG-3' (Underlined was the recognition site of restriction endonuclease Not I).

Using *Trichoderma reesei* genome as template, xylanase gene was amplified using the primers Xyn-F1 and Xyn-R1. The amplification products were recovered, and then ligated into plasmid pEASY-T. After that, the plasmid was transformed into *E. coli* DH5α. Positive transformants were selected and verified by DNA sequencing. This xylanase was named Xyn, and its encoding polynucleotide sequence was shown in SEQ ID NO: 2 and the corresponding amino acid sequence was shown in SEQ ID NO: 1.

Example 2 Screening for Thermostable Mutants

Disulfide bridge (i.e., Cys-Cys bridge) can stabilize the structure of enzyme. A certain number of disulfide bridges are necessary to maintain the stability of enzyme. One or more disulfide bridges can be artificially introduced into the protein structure to improve the stability, especially thermostability of the protein, but the activity of the protein may be reduced.

The sequence and structure (Crystal structure PDB ID: 2JIC) of Xyn were analyzed and modified to improve the thermostability, such as introducing one or more non-natural disulfide bridge by site-directed mutagenesis. For example, the disulfide bridge T1C-T27C was introduced to stabilize the N-terminal region of Xyn, another disulfide bridge S109C-N153C was introduced to stabilize the α-helix region of Xyn, and the other disulfide bridge Q33C-T187C was introduced to stabilize the C-terminal region of Xyn.

The mutant with two disulfide bridges Q33C-T187C and S109C-N153C was named XynA1, of which the amino acid sequence was shown as SEQ ID NO: 3 and the polynucleotide sequence was shown as SEQ ID NO: 4. The mutant with three disulfide bridges Q33C-T187C, S109C-N153C and T1C-T27C was named XynA2, of which the amino acid sequence was shown as SEQ ID NO: 5 and the polynucleotide sequence was shown as SEQ ID NO: 6.

The polynucleotide sequences of XynA1 and XynA2 were synthesized by Shanghai Generay Biotech Co., Ltd, and amplified using the primers Xyn-F1 and Xyn-R1 in Example 1, which had an EcoR I restriction site and a Not I restriction site at the ends. PCR reaction conditions were: 94° C. for 5 min (1 cycle), 94° C. for 30 sec, 56° C. for 30 sec, 72° C. for 1 min (30 cycles), and 72° C. for 10 min. The results of agarose gel electrophoresis showed that the length of the gene fragments were both approximately 600 bp.

The wild-type xylanase (Xyn) gene fragment was amplified using the same method as described above.

Example 3 Construction of the Recombinant *P. pastoris* Strain

The gene fragments of XynA1 and XynA2 obtained above were ligated into plasmid pPIC-9k through EcoR I and Not I sites. The obtained expression vectors were named as pPIC9K-XynA1 and pPIC9K-XynA2.

The recombinant plasmids pPIC9K-XynA1 and pPIC9K-XynA2 were linearized by Sal I and transformed into host cells *Pichia pastoris* GS115 by electroporation. The recombinant strains *P. pastoris* GS115/pPIC9K-XynA1 and GS115/pPIC9K-XynA2 were obtained on MD plates. YPD plates containing different concentrations of geneticin were used to select transformants with multiple copies.

The transformants of the recombinant strains GS115/pPIC9K-XynA1 and GS115/pPIC9K-XynA2 were named *Pichia pastoris* XynA1 and *Pichia pastoris* XynA2, respectively. The above two transformants were inoculated into separate flasks with BMGY medium and cultured at 30° C. for 1 d with shaking at 250 rpm, and then the cultures were transferred to BMMY medium and cultured at 30° C. at 250 rpm. 0.5% methanol, as an inducer, was added every 24 h for 4 d. The cells were removed by centrifugation from the fermentation broth and the fermentation supernatants containing xylanase mutants XynA1 and XynA2 were retained. The results of SDS-PAGE showed that the molecular weight of XynA1 and XynA2 in the fermentation supernatants were both approximately 20.7 kDa.

The wild-type Xyn gene was transformed into the host cells Pichia pastoris GS115 using the same method as described above. The recombinant strain P. pastoris of the wild-type Xyn was named as Pichia pastoris Xyn. Pichia pastoris Xyn was cultivated by flask fermentation at 30° C. with shaking at 250 rpm. 0.5% methanol, as an inducer, was added every 24 h for 4 d. The cells were removed by centrifugation to obtain the fermentation supernatant containing Xyn.

(1) Definition of Xylanase Activity Unit

One unit of xylanase activity is defined as the amount of xylanase that generates 1 μmol of reducing sugars per minute from 5 mg/ml xylan solution at pH 5.5 and 37° C., which is indicated as U.

(2) Method for Detecting Xylanase Activity 2 ml of 1% xylan substrate (made in acetic acid-sodium acetate buffer at pH 5.5) is added into a tube and incubated at 37° C. for 10 min. And then 2 ml of xylanase solution diluted by acetic acid-sodium acetate buffer (pH 5.5) and equilibrated at 37° C. is added and mixed well. The mixture is incubated for 30 min at 37° C. precisely. The reaction is terminated by adding 5 ml of DNS solution and mixing. The tube is put into a boiling water bath for 5 minutes. After cooling down to room temperature with tap water, the volume in the tube is adjusted up to 25 ml by adding distilled water. The absorbance AE is measured at 540 nm using a standard blank sample as a blank control.

Calculation formula of enzyme activity:

$$X_D = \frac{[(A_E - A_B) \times K + C_0]}{M \times t} \times N \times 1000.$$

Wherein, $X_D$—the activity of xylanase in diluted solution, U/ml;
$A_E$—the absorbance value of enzyme solution;
$A_B$—the absorbance value of blank;
K—the slope of the standard curve;
Co—the intercept of the standard curve;
M—molar mass of xylan, 150.2 g/mol;
t—reaction time;
N—dilution factor;
1000—conversion factor, 1 mmol=1000 μmol.

(3) The Results of Xylanase Activity Detection

The xylanase activities of the fermentation supernatants of Pichia pastoris Xyn, XynA1 and XynA2 were detected by the method mentioned above. The results showed that the xylanase activities of Pichia pastoris Xyn, XynA1 and XynA2 were 115 U/ml, 104 U/mL and 71 U/mL, respectively.

Example 4 Large-Scale Fermentation Verification

P. pastoris Xyn, P. pastoris XynA1 and P. pastoris XynA2 were cultured in three separate 10 L fermenters with the fermentation medium containing: 1.1 g/L $CaSO_4$, 5.5 g/L $KH_2PO_4$, 55 g/L $NH_4H_2PO_4$, 20.3 g/L $K_2SO_4$, 16.4 g/L $MgSO_4$, 1.65 g/L KOH and 0.05% antifoam.

The fermentation parameters: pH 5.0, 30° C., agitation at 300 rpm, aeration at 1.0-1.5 v/v, and the dissolved oxygen kept above 20%.

There were three stages of the fermentation process. The first stage was for cell culture with 7% seed inoculated and cultured at 30° C. for 24-26 h until the supplement of glucose was finished. The second stage was for cell starvation with no more carbon source supplemented. This stage lasted about 30-60 min until the concentration of dissolved oxygen rose to 80%. The third stage was for inducing the expression of xylanase with methanol addition as an inducer in feed, and the concentration of dissolved oxygen maintained at more than 20%, which lasted about 150-180 h. After that, the fermentation broth was passed through a plate and frame filter to obtain crude enzyme solution.

The xylanase activities of the crude enzyme solutions were detected by the method described in Example 3. The results showed that the xylanase activities of the crude enzyme solutions of P. pastoris Xyn, P. pastoris XynA1 and P. pastoris XynA2 were 7030 U/ml, 6954 U/mL and 5507 U/mL, respectively.

Example 5 Thermostability Detection of Xylanse and Mutants

The crude enzyme solutions obtained in Example 4 were diluted with acetic acid-sodium acetate buffer (pH 5.5) to about 20 U/ml. The diluted enzyme solutions were treated at 65° C., 70° C., 75° C. and 80° C. for 5 min, respectively, and then the xylanase activity was detected. The activity of the untreated enzyme solution was set as 100%, and the residual xylanase activities were calculated. The results were shown in Table 1.

Residual xylanase activity (%)=(the xylanase activity of the treated enzyme solution/the xylanase activity of the untreated enzyme solution)× 100%.

TABLE 1

| | Residual xylanase activities | | | |
|---|---|---|---|---|
| Xylanase | Residual xylanase activity (after being treated at 65° C. for 5 min) | Residual xylanase activity (after being treated at 70° C. for 5 min) | Residual xylanase activity (after being treated at 75° C. for 5 min) | Residual xylanase activity (after being treated at 80° C. for 5 min) |
| Wild-tpye Xyn | 0 | 0 | 0 | 0 |
| Mutant XynA1 | 88.1#% | 81.9#% | 32.1#% | 3*% |
| Mutant XynA2 | 100#% | 100#% | 90.1#% | 75#% |

Notes:
Compared with wild-type xylanase,
*stands for P < 0.05;
stands for P < 0.01.

As shown in Table 1, compared with wild-type xylanase (Xyn), the mutant XynA1 with two extra disulfide bridges Q33C-T187C and S109C-N153C, and the mutant XynA2 with three extra disulfide bridges Q33C-T187C, S109C-N153C and T1C-T27C, both had higher heat resistance, especially the mutant XynA2. After being treated at 80° C. for 5 min, the residual activity of the mutant XynA2 was 75%, which was 72% higher than that of the mutant XynA1. Thus, the thermostability of xylanase can be greatly improved by introducing extra disulfide bridges, and the number of the disulfide bridges also obviously affects the thermostability.

As shown in Example 4, the enzyme activity of the mutant XynA1 with two extra disulfide bridges Q33C-T187C and S109C-N153C was equivalent to that of the wild-type xylanase in large-scale fermentation, While the enzyme activity of the mutant XynA2 with three extra disulfide bridges Q33C-T187C, S109C-N153C and T1C-T27C was reduced by 21.7%, compared with the wild-type xylanase.

Example 6 Screening and Identifying of the Point Mutations

In order to improve the thermostability of the mutant XynA1, a large number of point mutations obtained by random mutagenesis had been screened.

XynA1 gene was amplified using the primers Xyn-F1 and Xyn-R1 mentioned above by GeneMorph II random mutagenesis kit (Stratagene). The amplification products were recovered, digested with EcoR I and Not I and then ligated into EcoRI-NotI-digested plasmid pET21a. After that, the plasmid was transformed into E. coli BL21 (DE3) and then the recombinant E. coli cells were spread onto LB+Amp plates. After being incubated at 37° C., the colonies were transferred one by one into 96-well polypropylene microtiter plates containing LB+Amp medium with 150 μl of 0.1 mM IPTG in each well. The microtiter plates were incubated at 37° C. for 6 h with shaking at 220 rpm. The supernatants were removed from the fermentation broth by centrifugation. Afterwards the cells were re-suspended with buffer and repeated freeze-thawed to obtain xylanase-containing E. coli cell lysates.

300 of cell lysate of each well was transferred into two separate new 96-well plates, one of which was treated at 75° C. for 8 min, and the other was not. 30 μl of substrate was added into each well of the plates and incubated for 30 min at 37° C. The generated reducing sugar was detected by the DNS method, and the enzyme activities of different mutants after high temperature treatment were calculated.

Compared with XynA1, the thermostability of some mutants was not improved, such as the mutants comprising the point mutations selected from S39D, K55A, E106T and T108F. The thermostability or activities of some mutants were even worse, such as the mutants comprising the point mutations selected from N18A, N91K, S148I and A184V. Besides, there were some mutants with improved thermostability, but their enzymatic properties were significantly changed, which also didn't meet the requirements.

The residual xylanase activities of the mutants are shown in Table 2.

TABLE 2

Residual xylanase activities of the mutants

| Mutants | Residual xylanase activity (after being treated at 75° C. for 5 min) |
| --- | --- |
| XynA1 | 32.12% |
| XynA1/S39D | 27.99% |
| XynA1/K55A | 29.21% |
| XynA1/E106T | 29.73% |
| XynA1/T108F | 28.07% |
| XynA1/N18A | 19.83% |
| XynA1/N91K | 22.57% |
| XynA1/S148I | 25.63% |
| XynA1/A184V | 19.13% |

This invention provided three point mutations Q51N, H143K and Q161F, which could significantly improve the thermostability of XynA1, while had no negative effects on the high activities and original enzymatic properties of XynA1.

One mutant was named XynA1-Q51N with the mutation Q51N, of which the amino acid sequence was shown as SEQ ID NO: 7, and the polynucleotide sequence was shown as SEQ ID NO: 8.

Another mutant was named XynA1-H143K with the mutation H143K, of which the amino acid sequence was shown as SEQ ID NO: 9, and the polynucleotide sequence was shown as SEQ ID NO: 10.

The other mutant was named XynA1-Q161F with the mutation Q161F, of which the amino acid sequence was shown as SEQ ID NO: 11, and the polynucleotide sequence was shown as SEQ ID NO: 12.

The polynucleotide sequences of xylanase mutants mentioned above were synthesized by Shanghai Generay Biotech Co., Ltd.

The recombinant P. pastoris strains which express the above mutants were constructed and the thermostability of these xylanase mutants were detected by the methods described in examples 2-5. The results are shown in Table 3.

TABLE 3

The residual xylanase activities of the mutants

| Xylanase mutants | Residual xylanase activity (after being treated at 75° C. for 5 min) | Residual xylanase activity (after being treated at 80° C. for 5 min) | Residual xylanase activity (after being treated at 85° C. for 3 min) |
| --- | --- | --- | --- |
| XynA1 | 32.12% | 3.03% | 0 |
| XynA1-Q51N | 75.89#% | 2.11% | 0 |
| XynA1-H143K | 95.79#% | 1.38% | 0 |
| XynA1-Q161F | 87.49#% | 6.68*% | 0 |

Notes:
Compared with XynA1,
*stands for P < 0.05;
stands for P < 0.01.

As shown in Table 3, anyone of the three point mutations Q51N, H143K or Q161F could significantly improve the thermostability of the mutant XynA1. Compare with XynA1, the residual activities of the mutants XynA1-Q51N, XynA1-H143K and XynA1-Q161F were increased by 43.72%-63.62%. Among them, the mutant XynA1-H143K showed the highest residual enzyme activity of 95.79%, which was unexpected.

Example 7 Screening for High Thermostability Mutants with Combinations of Point Mutations The combinations of the point mutations selected from Q51N, H143K and Q161F were screened using the method described in Example 6. The thermostability of the new mutants was detected.

The results showed that, mutants with the combination of H143K+Q51N, H143K+Q161F, Q51N+Q161F, or H143K+Q51N+Q161F had higher heat resistance than the mutants with only one mutation selected from H143K, Q51N and Q161F.

Mutant with the combination of two mutations H143 and Q51N was named XynA1-H143K-Q51N, of which the amino acid sequence was shown as SEQ ID NO: 13, and one of the corresponding polynucleotide sequence was shown as SEQ ID NO: 14.

Mutant with the combination of two mutations H143 and Q161F was named XynA1-H143K-Q161F, of which the amino acid sequence was shown as SEQ ID NO: 15, and one of the corresponding polynucleotide sequence was shown as SEQ ID NO: 16.

Mutant with the combination of two mutations Q51N and Q161F was named XynA1-Q51N-Q161F, of which the amino acid sequence was shown as SEQ ID NO: 17, and one of the corresponding polynucleotide sequence was shown as SEQ ID NO: 18.

Mutant with the combination of three mutations H143K, Q51N and Q161F was named XynA1-H143K-Q51N-Q161F, of which the amino acid sequence was shown as SEQ ID NO: 19, and one of the corresponding polynucleotide sequence was shown as SEQ ID NO: 20.

The polynucleotide sequences of xylanase mutants mentioned above were synthesized by Shanghai Generay Biotech Co., Ltd.

The recombinant *P. pastoris* strains that express the above mutants were constructed and the thermostability of these xylanase mutants were detected by the methods described in examples 2-5. The results are shown in Table 4.

As shown in Table 4, the mutants with the combination of two or three mutations selected from Q51N, H143K and Q161F had higher heat resistance than the mutants XynA1-Q51N, XynA1-H143K or XynA1-Q161F with only one mutation. The residual enzyme activity of the mutant XynA1-H143K-Q51N-Q161F with three mutations remained 61.28% after being treated at 80° C. for 5 min and still remained 26.89% after being treated at 85° C. for 3 min, indicating that the thermostability of the mutant had been significantly improved.

Example 8 Thermostability of Xyna2 with Point Mutation

In order to improve the thermostability of the mutant XynA2, one or more mutations selected from Q51N, H143K and Q161F were introduced respectively.

Mutant with one mutation Q51N was named XynA2-Q51N, of which the amino acid sequence was shown as SEQ ID NO: 21, and one of the corresponding polynucleotide sequence was shown as SEQ ID NO: 22.

Mutant with one mutation H143K was named XynA2-H143K, of which the amino acid sequence was shown as SEQ ID NO: 23, and one of the corresponding polynucleotide sequence was shown as SEQ ID NO: 24.

Mutant with one mutation Q161F was named XynA2-Q161F, of which the amino acid sequence was shown as SEQ ID NO: 25, and one of the corresponding polynucleotide sequence was shown as SEQ ID NO: 26.

The polynucleotide sequences of the xylanase mutants mentioned above were synthesized by Shanghai Generay Biotech Co., Ltd.

The recombinant *P. pastoris* strains that express the above mutants were constructed and the thermostability of the mutants was detected by the methods described in examples 2-5. The results are shown in Table 5.

TABLE 5

The residual xylanase activities of the mutants

| Mutants | Residual xylanase activity (after being treated at 75° C. for 5 min) | Residual xylanase activity (after being treated at 80° C. for 5 min) | Residual xylanase activity (after being treated at 85° C. for 3 min) |
|---|---|---|---|
| XynA2 | 90.14% | 75.20% | 43.57% |
| XynA2-Q51N | 100#% | 92.56#% | 81.15#% |

TABLE 4

The residual xylanase activities of the mutants

| Mutants | Residual xylanase activity (after being treated at 75° C. for 5 min) | Residual xylanase activity (after being treated at 80° C. for 5 min) | Residual xylanase activity (after being treated at 85° C. for 3 min) |
|---|---|---|---|
| XynA1 | 32.12% | 3.03% | 0 |
| XynA1-Q51N | 75.89% | 2.11% | 0 |
| XynA1-H143K | 95.79% | 1.38% | 0 |
| XynA1-Q161F | 87.49% | 6.68% | 0 |
| XynA1-H143K-Q51N | 97.83*% | 19.78#% | 7.91#% |
| XynA1-H143K-Q161F | 100*% | 21.43#% | 8.13#% |
| XynA1-Q51N-Q161F | 90.78*% | 15.06#% | 6.05#% |
| XynA1-H143K-Q51N-Q161F | 100*% | 61.28#% | 26.89#% |

Notes:
Compared with XynA1-Q51N, XynA1-H143K and XynA1-Q161F, respectively.
*stands for P < 0.05;
stands for P < 0.01.

TABLE 5-continued

The residual xylanase activities of the mutants

| Mutants | Residual xylanase activity (after being treated at 75° C. for 5 min) | Residual xylanase activity (after being treated at 80° C. for 5 min) | Residual xylanase activity (after being treated at 85° C. for 3 min) |
|---|---|---|---|
| XynA2-H143K | 100#% | 99.78#% | 90.18#% |
| XynA2-Q161F | 100#% | 84.46*% | 70.2*% |

Notes:
Compared with XynA2,
*stands for P < 0.05;
stands for P < 0.01.

As shown in table 5, the introduction of mutation Q51N, H143K or Q161F could improve the thermostability of the mutant XynA2. Compare with XynA2, the residual activities of the mutants XynA2-Q51N, XynA2-H143K, or XynA2-Q161F with one mutation was increased by 9.26%-24.58% after being treated at 80° C. for 5 min and increased by 26.63%-46.61% after being treated at 85° C. for 3 min, giving a significant effect. Among them, the mutant XynA2-H143K with the mutation H143K had the highest heat resistance.

Furthermore, the combinations of two or three mutations selected from Q51N, H143K and Q161F were introduced to improve the thermostability of XynA2. The thermostability of the mutants was detected. The results showed that, the mutants with the combination selected from H143K+Q51N, H143K+Q161F, Q51N+Q161F and H143K+Q51N+Q161F had higher heat resistance than the mutants with only one mutation. The residual activities of the mutants with combination mutations remained 100% after being treated at 80° C. for 5 min and still over 95% after being treated at 85° C. for 3 min, indicating that the thermostability of the mutants had been significantly improved.

The xylanase mutants provided herein are described in detail. The principles and embodiments of the invention have been described with reference to specific examples, and the descriptions of the above embodiments are merely illustrative of the method and the core idea of the present invention. It is particularly to be noted that all similar substitutions and modifications without departing from the principle will be regarded as obvious to those skilled in the field and are considered to be fallen within the scope of the claims of the invention.

The invention claimed is:

1. A xylanase mutant, comprising an amino acid sequence selected from the group consisting of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

2. The xylanase mutant of claim 1, which comprises two disulfide bridges: Q33C-T187C and S109C-N153C, and the amino acid sequence thereof is shown as SEQ ID NO: 3.

3. The xylanase mutant of claim 1, which comprises three disulfide bridges: T1C-T27C, Q33C-T187C and S109C-N153C, and the amino acid sequence thereof is shown as SEQ ID NO: 5.

4. The xylanase mutant of claim 1, which comprises an amino acid sequence selected from the group consisting of SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NO: 25.

5. A DNA molecule comprising a polynucleotide sequence encoding the xylanase mutant of claim 1, wherein the polynucleotide sequence is selected from the group consisting of SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24 and SEQ ID NO: 26.

6. An expression vector comprising the DNA molecule of claim 5.

7. A host cell comprising the expression vector of claim 6.

8. A method of producing the xylanase mutant of claim 1, comprising:
　　Step 1: obtaining a DNA molecule encoding the xylanase mutant of claim 1;
　　Step 2: inserting the DNA molecule obtained by step 1 into an expression vector, constructing a recombinant expression vector, and transforming the recombinant expression vector into a host cell; and
　　Step 3: inducing the host cell containing the recombinant expression vector to express the xylanase mutant, and then isolating and purifying the xylanase mutant.

* * * * *

SEQUENCE LISTING

```
<160> NUMBER OF SEQ ID NOS: 26

<210> SEQ ID NO 1
<211> LENGTH: 189
<212> TYPE: PRT
<213> ORGANISM: Trichoderma reesei

<400> SEQUENCE: 1

Thr Ile Gln Pro Gly Thr Gly Tyr Asn Asn Gly Tyr Phe Tyr Ser Tyr
1               5                   10                  15

Trp Asn Asp Gly His Gly Val Thr Tyr Thr Asn Gly Pro Gly Gly
            20                  25                  30

Gln Phe Ser Val Asn Trp Ser Asn Ser Gly Asn Phe Val Gly Gly Lys
        35                  40                  45

Gly Trp Gln Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Ser Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Asn His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Thr Val Ser
            180                 185

<210> SEQ ID NO 2
```

<211> LENGTH: 567
<212> TYPE: DNA
<213> ORGANISM: Trichoderma reesei

<400> SEQUENCE: 2

```
actattcaac ctggaactgg atacaataac ggttatttct actcttactg gaacgatgga    60
catggaggtg tcacatacac taacggtcca ggtggacaat tctcagttaa ttggtctaac   120
tcaggaaatt tcgtcggagg taaaggatgg caaccaggaa ctaagaataa ggtcattaac   180
ttctcaggtt catataatcc aaacggaaac tcctacttgt ccgtttacgg ttggtcccgt   240
aacccttga tcgaatatta cattgttgaa aacttcggta cttataatcc ttccaccgga   300
gccactaagc tgggtgaagt cacctctgat ggttcagttt atgatatata tagaacacaa   360
cgtgttaatc aaccatccat catcggtaca gctacatttt accaatattg gtctgttagg   420
cgtaaccatc gtagctccgg ttccgtcaac accgcaaatc atttcaatgc ttgggcccaa   480
caaggactga ccttaggtac tatggattat caaatcgtcg ctgtcgaagg atacttctcc   540
tctggatctg cctctatcac agtctca                                       567
```

<210> SEQ ID NO 3
<211> LENGTH: 189
<212> TYPE: PRT
<213> ORGANISM: Artificial
<220> FEATURE:
<223> OTHER INFORMATION: Xylanase mutant (Q33C-T187C, S109C-N153C)

<400> SEQUENCE: 3

```
Thr Ile Gln Pro Gly Thr Gly Tyr Asn Asn Gly Tyr Phe Tyr Ser Tyr
 1               5                  10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Gln Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 4
<211> LENGTH: 567
<212> TYPE: DNA
<213> ORGANISM: Artificial
<220> FEATURE:
<223> OTHER INFORMATION: Xylanase mutant

<400> SEQUENCE: 4

```
actattcaac ctggaactgg atacaataac ggttatttct actcttactg gaacgatgga    60
catggaggtg tcacatacac taacggtcca ggtggatgtt tctcagttaa ttggtctaac   120
tcaggaaatt tcgtcggagg taaaggatgg caaccaggaa ctaagaataa ggtcattaac   180
ttctcaggtt catataatcc aaacggaaac tcctacttgt ccgtttacgg ttggtcccgt   240
aacccttga tcgaatatta cattgttgaa aacttcggta cttataatcc ttccaccgga   300
gccactaagc tgggtgaagt cacctgtgat ggttcagttt atgatatata tagaacacaa   360
cgtgttaatc aaccatccat catcggtaca gctacatttt accaatattg gtctgttagg   420
cgtaaccatc gtagctccgg ttccgtcaac accgcatgtc atttcaatgc ttgggcccaa   480
caaggactga ccttaggtac tatggattat caaatcgtcg ctgtcgaagg atacttctcc   540
tctggatctg cctctatctg tgtctca                                       567
```

<210> SEQ ID NO 5
<211> LENGTH: 189
<212> TYPE: PRT
<213> ORGANISM: Artificial
<220> FEATURE:
<223> OTHER INFORMATION: Xylanase mutant (T1C-T27C, Q33C-T187C, S109C-N153C)

<400> SEQUENCE: 5

```
Cys Ile Gln Pro Gly Thr Gly Tyr Asn Asn Gly Tyr Phe Tyr Ser Tyr
  1               5                  10                  15

Trp Asn Asp Gly His Gly Gly Val Thr Tyr Cys Asn Gly Pro Gly Gly
             20                  25                  30

Cys Phe Ser Val Asn Trp Ser Asn Ser Gly Asn Phe Val Gly Gly Lys
         35                  40                  45

Gly Trp Gln Pro Gly Thr Lys Asn Lys Val Ile Asn Phe Ser Gly Ser
     50                  55                  60

Tyr Asn Pro Asn Gly Asn Ser Tyr Leu Ser Val Tyr Gly Trp Ser Arg
 65                  70                  75                  80

Asn Pro Leu Ile Glu Tyr Tyr Ile Val Glu Asn Phe Gly Thr Tyr Asn
                 85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 6
<211> LENGTH: 567
<212> TYPE: DNA
<213> ORGANISM: Artificial
<220> FEATURE:
<223> OTHER INFORMATION: Xylanase mutant

<400> SEQUENCE: 6

```
tgtattcaac ctggaactgg atacaataac ggttatttct actcttactg gaacgatgga      60
catggaggtg tcacatactg taacggtcca ggtggatgtt tctcagttaa ttggtctaac     120
tcaggaaatt tcgtcggagg taaggatgg caaccaggaa ctaagaataa ggtcattaac     180
ttctcaggtt catataatcc aaacggaaac tcctacttgt ccgtttacgg ttggtcccgt     240 aacccttga tcgaatatta cattgttgaa aacttcggta cttataatcc ttccaccgga     300
gccactaagc tgggtgaagt cacctgtgat ggttcagttt atgatatata tagaacacaa     360
cgtgttaatc aaccatccat catcggtaca gctacatttt accaatattg gtctgttagg     420
cgtaaccatc gtagctccgg ttccgtcaac accgcatgtc atttcaatgc ttgggcccaa     480
caaggactga ccttaggtac tatggattat caaatcgtcg ctgtcgaagg atacttctcc     540
tctggatctg cctctatctg tgtctca                                         567
```

<210> SEQ ID NO 7
<211> LENGTH: 189
<212> TYPE: PRT
<213> ORGANISM: Artificial
<220> FEATURE:
<223> OTHER INFORMATION: Xylanase mutant (Q33C-T187C, S109C-N153C, Q51N)

<400> SEQUENCE: 7

```
Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
                20                  25                  30

Cys Phe Ser Val Asn Trp Ser Asn Ser Gly Asn Phe Val Gly Gly Lys
            35                  40                  45

Gly Trp Asn Pro Gly Thr Lys Asn Lys Val Ile Asn Phe Ser Gly Ser
        50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 8
<211> LENGTH: 567
<212> TYPE: DNA
<213> ORGANISM: Artificial
<220> FEATURE:
<223> OTHER INFORMATION: Xylanase mutant

<400> SEQUENCE: 8

```
actattcaac ctggaactgg atacaataac ggttatttct actcttactg gaacgatgga      60
```

```
catggaggtg tcacatacac taacggtcca ggtggatgtt tctcagttaa ttggtctaac    120
tcaggaaatt tcgtcggagg taaaggatgg aacccaggaa ctaagaataa ggtcattaac    180
ttctcaggtt catataatcc aaacggaaac tcctacttgt ccgtttacgg ttggtcccgt    240 aacccttga tcgaatatta cattgttgaa aacttcggta cttataatcc ttccaccgga    300
gccactaagc tgggtgaagt cacctgtgat ggttcagttt atgatatata tagaacacaa    360
cgtgttaatc aaccatccat catcggtaca gctacatttt accaatattg gtctgttagg    420
cgtaaccatc gtagctccgg ttccgtcaac accgcatgtc atttcaatgc ttgggcccaa    480
caaggactga ccttaggtac tatggattat caaatcgtcg ctgtcgaagg atacttctcc    540
tctggatctg cctctatctg tgtctca                                         567
```

<210> SEQ ID NO 9
<211> LENGTH: 189
<212> TYPE: PRT
<213> ORGANISM: Artificial
<220> FEATURE:
<223> OTHER INFORMATION: Xylanase mutant (Q33C-T187C, S109C-N153C, H143K)

<400> SEQUENCE: 9

```
Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Gln Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn Lys Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 10
<211> LENGTH: 567
<212> TYPE: DNA
<213> ORGANISM: Artificial
<220> FEATURE:
<223> OTHER INFORMATION: Xylanase mutant

<400> SEQUENCE: 10

```
actattcaac ctggaactgg atacaataac ggttatttct actcttactg gaacgatgga     60
catggaggtg tcacatacac taacggtcca ggtggatgtt tctcagttaa ttggtctaac    120
```

```
tcaggaaatt tcgtcggagg taaaggatgg caaccaggaa ctaagaataa ggtcattaac        180
ttctcaggtt catataatcc aaacggaaac tcctacttgt ccgtttacgg ttggtcccgt        240 aacccttttga tcgaatatta cattgttgaa aacttcggta cttataatcc ttccaccgga       300
gccactaagc tgggtgaagt cacctgtgat ggttcagttt atgatatata tagaacacaa        360
cgtgttaatc aaccatccat catcggtaca gctacatttt accaatattg gtctgttagg        420
cgtaacaagc gtagctccgg ttccgtcaac accgcatgtc atttcaatgc ttgggcccaa        480
caaggactga ccttaggtac tatggattat caaatcgtcg ctgtcgaagg atacttctcc       540
tctggatctg cctctatctg tgtctca                                            567
```

```
<210> SEQ ID NO 11
<211> LENGTH: 189
<212> TYPE: PRT
<213> ORGANISM: Artificial
<220> FEATURE:
<223> OTHER INFORMATION: Xylanase mutant (Q33C-T187C, S109C-N153C,
      Q161F)

<400> SEQUENCE: 11

Thr Ile Gln Pro Gly Thr Gly Tyr Asn Asn Gly Tyr Phe Tyr Ser Tyr
  1               5                  10                  15

Trp Asn Asp Gly His Gly Gly Val Thr Tyr Thr Asn Gly Pro Gly Gly
             20                  25                  30

Cys Phe Ser Val Asn Trp Ser Asn Ser Gly Asn Phe Val Gly Gly Lys
         35                  40                  45

Gly Trp Gln Pro Gly Thr Lys Asn Lys Val Ile Asn Phe Ser Gly Ser
     50                  55                  60

Tyr Asn Pro Asn Gly Asn Ser Tyr Leu Ser Val Tyr Gly Trp Ser Arg
 65                  70                  75                  80

Asn Pro Leu Ile Glu Tyr Tyr Ile Val Glu Asn Phe Gly Thr Tyr Asn
                 85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Phe Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

```
<210> SEQ ID NO 12
<211> LENGTH: 567
<212> TYPE: DNA
<213> ORGANISM: Artificial
<220> FEATURE:
<223> OTHER INFORMATION: Xylanase mutant

<400> SEQUENCE: 12
actattcaac ctggaactgg atacaataac ggttatttct actcttactg gaacgatgga         60
catggaggtg tcatatacac taacggtcca ggtggatgtt tctcagttaa ttggtctaac       120
tcaggaaatt tcgtcggagg taaaggatgg caaccaggaa ctaagaataa ggtcattaac       180
```

```
ttctcaggtt catataatcc aaacggaaac tcctacttgt ccgtttacgg ttggtcccgt    240 aacccttga tcgaatatta cattgttgaa aacttcggta cttataatcc ttccaccgga    300
gccactaagc tgggtgaagt cacctgtgat ggttcagttt atgatatata tagaacacaa    360
cgtgttaatc aaccatccat catcggtaca gctacatttt accaatattg gtctgttagg    420
cgtaaccatc gtagctccgg ttccgtcaac accgcatgtc atttcaatgc ttgggcccaa    480
ttcggactga ccttaggtac tatggattat caaatcgtcg ctgtcgaagg atacttctcc    540
tctggatctg cctctatctg tgtctca                                       567
```

```
<210> SEQ ID NO 13
<211> LENGTH: 189
<212> TYPE: PRT
<213> ORGANISM: Artificial
<220> FEATURE:
<223> OTHER INFORMATION: Xylanase mutant (Q33C-T187C, S109C-N153C, Q51N,
      H143K)

<400> SEQUENCE: 13
```

Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Asn Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn Lys Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185

```
<210> SEQ ID NO 14
<211> LENGTH: 567
<212> TYPE: DNA
<213> ORGANISM: Artificial
<220> FEATURE:
<223> OTHER INFORMATION: Xylanase mutant

<400> SEQUENCE: 14
actattcaac ctggaactgg atacaataac ggttatttct actcttactg gaacgatgga    60
catggaggtg tcacatacac taacggtcca ggtggatgtt tctcagttaa ttggtctaac    120
tcaggaaatt tcgtcggagg taaggatgg aacccaggaa ctaagaataa ggtcattaac    180
ttctcaggtt catataatcc aaacggaaac tcctacttgt ccgtttacgg ttggtcccgt    240
```

```
aaccctttga tcgaatatta cattgttgaa aacttcggta cttataatcc ttccaccgga    300
gccactaagc tgggtgaagt cacctgtgat ggttcagttt atgatatata tagaacacaa    360
cgtgttaatc aaccatccat catcggtaca gctacatttt accaatattg gtctgttagg    420
cgtaacaagc gtagctccgg ttccgtcaac accgcatgtc atttcaatgc ttgggcccaa    480
caaggactga ccttaggtac tatggattat caaatcgtcg ctgtcgaagg atacttctcc    540
tctggatctg cctctatctg tgtctca                                        567
```

```
<210> SEQ ID NO 15
<211> LENGTH: 189
<212> TYPE: PRT
<213> ORGANISM: Artificial
<220> FEATURE:
<223> OTHER INFORMATION: Xylanase mutant (Q33C-T187C, S109C-N153C,
      H143K, Q161F)

<400> SEQUENCE: 15
```

```
Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Gln Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn Lys Arg
    130                 135                 140

Ser Ser Gly Ser Val Asn Thr Ala Cys His Phe Asn Ala Trp Ala Gln
145                 150                 155                 160

Phe Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

```
<210> SEQ ID NO 16
<211> LENGTH: 567
<212> TYPE: DNA
<213> ORGANISM: Artificial
<220> FEATURE:
<223> OTHER INFORMATION: Xylanase mutant

<400> SEQUENCE: 16
```

```
actattcaac ctggaactgg atacaataac ggttatttct actcttactg gaacgatgga     60
catggaggtg tcacatacac taacggtcca ggtggatgtt tctcagttaa ttggtctaac    120
tcaggaaatt tcgtcggagg taaggatggc aaccaggaa ctaagaataa ggtcattaac    180
ttctcaggtt catataatcc aaacggaaac tcctacttgt ccgtttacgg ttggtcccgt    240
aaccctttga tcgaatatta cattgttgaa aacttcggta cttataatcc ttccaccgga    300
```

```
gccactaagc tgggtgaagt cacctgtgat ggttcagttt atgatatata tagaacacaa    360
cgtgttaatc aaccatccat catcggtaca gctacatttt accaatattg gtctgttagg    420
cgtaacaagc gtagctccgg ttccgtcaac accgcatgtc atttcaatgc ttgggcccaa    480
ttcggactga ccttaggtac tatggattat caaatcgtcg ctgtcgaagg atacttctcc    540
tctggatctg cctctatctg tgtctca                                        567
```

<210> SEQ ID NO 17
<211> LENGTH: 189
<212> TYPE: PRT
<213> ORGANISM: Artificial
<220> FEATURE:
<223> OTHER INFORMATION: Xylanase mutant (Q33C-T187C, S109C-N153C, Q51N, Q161F)

<400> SEQUENCE: 17

```
Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Asn Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Phe Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 18
<211> LENGTH: 567
<212> TYPE: DNA
<213> ORGANISM: Artificial
<220> FEATURE:
<223> OTHER INFORMATION: Xylanase mutant

<400> SEQUENCE: 18

```
actattcaac ctggaactgg atacaataac ggttatttct actcttactg gaacgatgga     60
catggaggtg tcacatacac taacggtcca ggtggatgtt tctcagttaa ttggtctaac    120
tcaggaaatt tcgtcggagg taaaggatgg aacccaggaa ctaagaataa ggtcattaac    180
ttctcaggtt catataatcc aaacggaaac tcctacttgt ccgtttacgg ttggtcccgt    240 aacccttga tcgaatatta cattgttgaa aacttcggta cttataatcc ttccaccgga    300
gccactaagc tgggtgaagt cacctgtgat ggttcagttt atgatatata tagaacacaa    360
```

```
cgtgttaatc aaccatccat catcggtaca gctacatttt accaatattg gtctgttagg      420
cgtaaccatc gtagctccgg ttccgtcaac accgcatgtc atttcaatgc ttgggcccaa      480
ttcggactga ccttaggtac tatggattat caaatcgtcg ctgtcgaagg atacttctcc      540
tctggatctg cctctatctg tgtctca                                         567
```

<210> SEQ ID NO 19
<211> LENGTH: 189
<212> TYPE: PRT
<213> ORGANISM: Artificial
<220> FEATURE:
<223> OTHER INFORMATION: Xylanase mutant (Q33C-T187C, S109C-N153C, Q51N, H143K, Q161F)

<400> SEQUENCE: 19

```
Thr Ile Gln Pro Gly Thr Gly Tyr Asn Asn Gly Tyr Phe Tyr Ser Tyr
1               5                   10                  15

Trp Asn Asp Gly His Gly Gly Val Thr Tyr Thr Asn Gly Pro Gly Gly
            20                  25                  30

Cys Phe Ser Val Asn Trp Ser Asn Ser Gly Asn Phe Val Gly Gly Lys
        35                  40                  45

Gly Trp Asn Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn Lys Arg
    130                 135                 140

Ser Ser Gly Ser Val Asn Thr Ala Cys His Phe Asn Ala Trp Ala Gln
145                 150                 155                 160

Phe Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185
```

<210> SEQ ID NO 20
<211> LENGTH: 567
<212> TYPE: DNA
<213> ORGANISM: Artificial
<220> FEATURE:
<223> OTHER INFORMATION: Xylanase mutant

<400> SEQUENCE: 20

```
actattcaac ctggaactgg atacaataac ggttatttct actcttactg gaacgatgga      60
catggaggtg tcacatacac taacggtcca ggtggatgtt tctcagttaa ttggtctaac     120
tcaggaaatt tcgtcggagg taaggatgg aacccaggaa ctaagaataa ggtcattaac     180
ttctcaggtt catataatcc aaacggaaac tcctacttgt ccgtttacgg ttggtcccgt     240
aaccctttga tcgaatatta cattgttgaa aacttcggta cttataatcc ttccaccgga     300
gccactaagc tgggtgaagt cacctgtgat ggttcagttt atgatatata tagaacacaa     360
cgtgttaatc aaccatccat catcggtaca gctacatttt accaatattg gtctgttagg     420
```
cgtaacaagc gtagctccgg ttccgtcaac accgcatgtc atttcaatgc ttgggcccaa    480
ttcggactga ccttaggtac tatggattat caaatcgtcg ctgtcgaagg atacttctcc    540
tctggatctg cctctatctg tgtctca    567

<210> SEQ ID NO 21
<211> LENGTH: 188
<212> TYPE: PRT
<213> ORGANISM: Artificial
<220> FEATURE:
<223> OTHER INFORMATION: Xylanase mutant (T1C-T27C, Q33C-T187C,
      S109C-N153C, Q51N)

<400> SEQUENCE: 21

Cys Ile Gln Pro Gly Thr Gly Tyr Asn Asn Gly Tyr Phe Tyr Ser Tyr
1               5                   10                  15

Trp Asn Asp Gly His Gly Gly Val Thr Tyr Cys Asn Gly Pro Gly Gly
            20                  25                  30

Cys Phe Ser Val Asn Trp Ser Asn Ser Gly Asn Phe Val Gly Gly Lys
        35                  40                  45

Gly Trp Asn Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn His Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val
            180                 185

<210> SEQ ID NO 22
<211> LENGTH: 567
<212> TYPE: DNA
<213> ORGANISM: Artificial
<220> FEATURE:
<223> OTHER INFORMATION: Xylanase mutant

<400> SEQUENCE: 22
tgtattcaac ctggaactgg atacaataac ggttatttct actcttactg gaacgatgga    60
catggaggtg tcacatactg taacggtcca ggtggatgtt tctcagttaa ttggtctaac    120
tcaggaaatt tcgtcggagg taaggatgg aacccaggaa ctaagaataa ggtcattaac    180
ttctcaggtt catataatcc aaacggaaac tcctacttgt ccgtttacgg ttggtcccgt    240 aacccttga tcgaatatta cattgttgaa aacttcggta cttataatcc ttccaccgga    300
gccactaagc tgggtgaagt cacctgtgat ggttcagttt atgatatata tagaacacaa    360
cgtgttaatc aaccatccat catcggtaca gctacatttt accaatattg gtctgttagg    420
cgtaaccatc gtagctccgg ttccgtcaac accgcatgtc atttcaatgc ttgggcccaa    480
caaggactga ccttaggtac tatgggattat caaatcgtcg ctgtcgaagg atacttctcc     540
tctggatctg cctctatctg tgtctca     567

<210> SEQ ID NO 23
<211> LENGTH: 189
<212> TYPE: PRT
<213> ORGANISM: Artificial
<220> FEATURE:
<223> OTHER INFORMATION: Xylanase mutant (T1C-T27C, Q33C-T187C,
      S109C-N153C, H143K)

<400> SEQUENCE: 23

Cys Ile Gln Pro Gly Thr Gly Tyr Asn Asn Gly Tyr Phe Tyr Ser Tyr
1               5                   10                  15

Trp Asn Asp Gly His Gly Gly Val Thr Tyr Cys Asn Gly Pro Gly Gly
            20                  25                  30

Cys Phe Ser Val Asn Trp Ser Asn Ser Gly Asn Phe Val Gly Gly Lys
        35                  40                  45

Gly Trp Gln Pro Gly Thr Lys Asn Lys Val Ile Asn Phe Ser Gly Ser
    50                  55                  60

Tyr Asn Pro Asn Gly Asn Ser Tyr Leu Ser Val Tyr Gly Trp Ser Arg
65                  70                  75                  80

Asn Pro Leu Ile Glu Tyr Tyr Ile Val Glu Asn Phe Gly Thr Tyr Asn
                85                  90                  95

Pro Ser Thr Gly Ala Thr Lys Leu Gly Glu Val Thr Cys Asp Gly Ser
            100                 105                 110

Val Tyr Asp Ile Tyr Arg Thr Gln Arg Val Asn Gln Pro Ser Ile Ile
        115                 120                 125

Gly Thr Ala Thr Phe Tyr Gln Tyr Trp Ser Val Arg Arg Asn Lys Arg
    130                 135                 140

Ser Ser Gly Ser Val Asn Thr Ala Cys His Phe Asn Ala Trp Ala Gln
145                 150                 155                 160

Gln Gly Leu Thr Leu Gly Thr Met Asp Tyr Gln Ile Val Ala Val Glu
                165                 170                 175

Gly Tyr Phe Ser Ser Gly Ser Ala Ser Ile Cys Val Ser
            180                 185

<210> SEQ ID NO 24
<211> LENGTH: 567
<212> TYPE: DNA
<213> ORGANISM: Artificial
<220> FEATURE:
<223> OTHER INFORMATION: Xylanase mutant

<400> SEQUENCE: 24
tgtattcaac ctggaactgg atacaataac ggttatttct actcttactg gaacgatgga     60
catggaggtg tcacatactg taacggtcca ggtggatgtt tctcagttaa ttggtctaac    120
tcaggaaatt tcgtcggagg taaggatgg caaccaggaa ctaagaataa ggtcattaac    180
ttctcaggtt catataatcc aaacggaaac tcctacttgt ccgtttacgg ttggtcccgt    240
aaccctttga tcgaatatta cattgttgaa aacttcggta cttataatcc ttccaccgga    300
gccactaagc tgggtgaagt cacctgtgat ggttcagttt atgatatata tagaacacaa    360
cgtgttaatc aaccatccat catcggtaca gctacatttt accaatattg gtctgttagg    420
cgtaacaagc gtagctccgg ttccgtcaac accgcatgtc atttcaatgc ttgggcccaa    480
caaggactga ccttaggtac tatggattat caaatcgtcg ctgtcgaagg atacttctcc    540
tctggatctg cctctatctg tgtctca 567

<210> SEQ ID NO 25
<211> LENGTH: 189
<212> TYPE: PRT
<213> ORGANISM: Artificial
<220> FEATURE:
<223> OTHER INFORMATION: Xylanase mutant (T1C-T27C,Q33C-T187C, S109C-N153C, Q161F)

<400> SEQUENCE: 25

```
Cys Ile Gln Pro Gly Thr Gly Tyr Asn Asn Gly Tyr Phe Tyr Ser Tyr
  1               5                  10                  15
Trp Asn Asp Gly His Gly Gly Val Thr Tyr Cys Asn Gly Pro Gly Gly
             20                  25                  30
Cys Phe Ser Val Asn Trp Ser Asn Ser Gly Asn Phe Val Gly Gly Lys
         35                  40                  45
Gly Trp Gln Pro Gly Thr Lys Asn Lys Val Ile Asn Phe Ser Gly Ser
     50                  55                  60
Tyr Asn Pro Asn Gly Asn Ser Tyr Leu Ser Val Tyr Gly Trp Ser Arg
 65                  70                  75                  80
Asn Pro Leu Ile Glu Tyr Tyr Ile Val Glu Asn Phe Gly Thr Tyr Asn
                 85                  90                  95
Pro Ser Thr Gly Ala Thr Lys Leu Gly Glu Val Thr Cys Asp Gly Ser
            100                 105                 110
Val Tyr Asp Ile Tyr Arg Thr Gln Arg Val Asn Gln Pro Ser Ile Ile
        115                 120                 125
Gly Thr Ala Thr Phe Tyr Gln Tyr Trp Ser Val Arg Arg Asn His Arg
    130                 135                 140
Ser Ser Gly Ser Val Asn Thr Ala Cys His Phe Asn Ala Trp Ala Gln
145                 150                 155                 160
Phe Gly Leu Thr Leu Gly Thr Met Asp Tyr Gln Ile Val Ala Val Glu
                165                 170                 175
Gly Tyr Phe Ser Ser Gly Ser Ala Ser Ile Cys Val Ser
            180                 185
```

<210> SEQ ID NO 26
<211> LENGTH: 567
<212> TYPE: DNA
<213> ORGANISM: Artificial
<220> FEATURE:
<223> OTHER INFORMATION: Xylanase mutant

<400> SEQUENCE: 26
tgtattcaac ctggaactgg atacaataac ggttatttct actcttactg gaacgatgga 60
catggaggtg tcacatactg taacggtcca ggtggatgtt tctcagttaa ttggtctaac 120
tcaggaaatt tcgtcggagg taaaggatgg caaccaggaa ctaagaataa ggtcattaac 180
ttctcaggtt catataatcc aaacggaaac tcctacttgt ccgtttacgg ttggtcccgt 240
aacccttga tcgaatatta cattgttgaa aacttcggta cttataatcc ttccaccgga 300
gccactaagc tgggtgaagt cacctgtgat ggttcagttt atgatatata tagaacacaa 360
cgtgttaatc aaccatccat catcggtaca gctacttttt accaatattg gtctgttagg 420
cgtaaccatc gtagctccgg ttccgtcaac accgcatgtc atttcaatgc ttgggcccaa 480
aacggactga cctaggtac tatgattat caaatcgtcg ctgtcgaagg atacttctcc 540
tctggatctg cctctatctg tgtctca 567